United States Patent [19]

Morrison

[11] Patent Number: 4,686,316
[45] Date of Patent: Aug. 11, 1987

[54] PRODUCTION OF BUTANES FROM PROPANE

[75] Inventor: Roger A. Morrison, Deptford, N.J.

[73] Assignee: Mobil Oil Corporation, New York, N.Y.

[21] Appl. No.: 845,284

[22] Filed: Mar. 28, 1986

[51] Int. Cl.⁴ .................................................. C07C 6/10
[52] U.S. Cl. ...................................... 585/708; 585/752
[58] Field of Search .................... 585/708, 78 M, 752, 585/643

[56] References Cited

U.S. PATENT DOCUMENTS 3,668,268  6/1972  Mulasky ............................. 585/708
3,668,269  6/1972  Chloupek ........................... 585/708
3,812,199  5/1974  Chen et al. ......................... 585/708
3,914,331  10/1975 Lucki et al. ........................ 585/708
3,953,537  4/1976  Chloupek et al. .................. 585/708

OTHER PUBLICATIONS

Frillette et al, J. Catalysis, 67(1), 1981, pp. 218-222.
Engelen et al, Applied Catalysis, 19, pp. 153-163 (1985).

Primary Examiner—Asok Pal
Attorney, Agent, or Firm—Alexander J. McKillop; Michael G. Gilman; Dennis P. Santini

[57] ABSTRACT

Process for converting propane to a mixture of normal butane and isobutane by contact with a ZSM-5 type zeolite in the absence of added hydrogen. The isobutane formed may be used to manufacture alkylate for motor fuel.

10 Claims, No Drawings

PRODUCTION OF BUTANES FROM PROPANE

FIELD OF THE INVENTION

This invention is concerned with the production of butanes from propane. In particular, it is concerned with the catalytic conversion of propane in the absence of added hydrogen by contact with a catalyst of the ZSM-5 type, as more fully described hereinbelow.

BACKGROUND OF THE INVENTION

Zeolite ZSM-5, described in U.S. Pat. No. 3,702,886 to Argauer et al., is known to be a shape-selective zeolite having an intermediate pore size, i.e. a pore size smaller than Zeolite X or Y but larger than Zeolite A. Since its discovery, ZSM-5 and related zeolites, more fully defined below, has been shown to be capable of efficiently catalyzing some unusual hydrocarbon (and other) conversions, and a large number of patents have issued describing such conversions. For example, U.S. Pat. No. 4,120,910 to Chu describes the conversion of ethane to aromatic hydrocarbons by contact at about 1100° F. At much lower temperatures, such as at about 650° F., it is known the higher linear and singly methyl-branched alkanes having six or more carbon atoms may be reacted with benzene, for example, to form alkylbenzenes and lower alkanes, presumably by reaction of olefins formed in situ from the alkane (by acid cracking) with the benzene.

It is generally recognized by those skilled in the art that alkanes having eight or more carbon atoms are relatively easily cracked to lower molecular weight hydrocarbons when contacted with an acidic catalyst, and that the reaction proceeds with very little disproportionation to paraffins of higher molecular weight than the charge. It is also generally known that as the molecular weight of the charged paraffin decreases, the reactivity of the paraffin also decreases.

BRIEF SUMMARY OF THE INVENTION

It has now been found that propane is effectively converted with unexpectedly high selectivity to a mixture of normal butane and isobutane by contact with certain intermediate pore size zeolites, as more fully described hereinbelow. In particular, this invention provides a process for the production of butanes from propane, which process comprises contacting in the absence of added hydrogen and at a pressure of at least about 50 psig a feed consisting essentially of propane with a catalyst comprising a crystalline zeolite having a silica-to-alumina ratio of at least 12 and a Constraint Index of 1 to 12, said contacting being conducted under a combination of conditions of temperature, pressure, and WHSV effective to convert up to about 25 wt% of said propane to a mixture of hydrocarbons that contain butanes in an amount equal to at least 35 wt% of said converted propane. The total effluent from the catalytic reactor will contain unreacted propane, which may be separated and recycled. Such separation step simultaneously provides a hydrocarbon fraction that may contain as much as 80–90 wt% of mixed butanes from which an isobutane fraction may be obtained that is useful for conversion to alkylate blending stock for gasoline.

In effect, the process of this invention provides the petroleum refiner with a method for converting propane by-product, which has a low economic value and is often burned for fuel, to much more valuable high-octane alkylate for blending in gasoline.

The process of this invention is advantageous in that it requires a very simple process configuration. Only liquid propane is charged to the reactor, and the total reaction effluent may be separated by conventional means to recover unreacted propane for recycle. The catalyst bed may be a simple fixed bed, although a fluidized bed may be used. No hydrogen is required, and indeed is detrimental, as will be shown hereinbelow. Long cycle life is indicated, so that frequent regeneration is not needed.

DETAILED DESCRIPTION AND BEST MODE

The propane feed to the process of this invention consists essentially of a hydrocarbon mixture having a propane content of at least about 95%. Suitable sources for the propane feed include petroleum refinery streams and natural gas liquids.

For purposes of this invention, the catalytic conversion is effected under a combination of conditions of temperature, pressure, and weight hourly space velocity (WHSV) effective to convert up to 25 wt% of the propane feed, and effective to provide a selectivity to butanes of at least 35 wt%, preferably in the range of about 45 to about 95 wt%, the remainder being converted principally to other C1 to C5 alkanes, as illustrated hereinafter by example. In general, increase of temperature, or of pressure, or decrease of space velocity all serve to increase conversion, so that many combinations of these parameters will produce conversion and selectivity within the desired range. It is evident that under such conditions it becomes difficult to specify with any simplicity operable ranges for the three individual parameters that are independent of one another. In general, however, the effective combinations will have individual parameters falling within the ranges shown below:

|  | Broad | Preferred |
|---|---|---|
| Temperature, | 500–900° F. | 600–800° F. |
| Pressure, psig | 50–1500 | 400–1000 |
| WHSV | 0.1 to 10 | 0.4 to 5.0 |

Within the described constraints, useful yields of isobutane per pass are achieved without encountering rapid aging.

The catalysts useful in the process of this invention contain a zeolite sometimes referred to as of the ZSM-5 type.

The members of the class of zeolites useful for such catalysts have an effective pore size of generally from about 5 to about 8 angstroms, such as to freely sorb normal hexane. In addition, the structure must provide constrained access to larger molecules. It is sometimes possible to judge from a known crystal structure whether such constrained access exists. For example, if the only pore windows in a crystal are formed by 8-membered rings of silicon and aluminum atoms, then access by molecules of larger cross-section than normal hexane is excluded and the zeolite is not of the desired type. Windows of 10-membered are preferred, although, in some instances, excessive puckering of the rings or pore blockage may render these zeolites ineffective.

Although 12-membered rings in theory would not offer sufficient constraint to produce advantageous conversions, it is noted that the puckered 12-ring structure of TMA offretite does show some constrained access. Other 12-ring structures may exist which may be operative for other reasons, and therefore, it is not the present intention to entirely judge the usefulness of the particular zeolite solely from theoretical structural considerations.

A convenient measure of the extent to which a zeolite provides control to molecules of varying sizes to its internal structure is the Constraint Index of the zeolite. Zeolites which provide a highly restricted access to and egress from its internal structure have a high value for the Constraint Index, and zeolites of this kind usually have pores of small size, e.g. less than 5 angstroms. On the other hand, zeolites which provide relatively free access to the internal zeolite structure have a low value for the Constraint Index, and usually have pores of large size, e.g. greater than 8 angstroms. The method by which Constraint Index is determined is described fully in U.S. Pat. No. 4,016,218, incorporated herein by reference for details of the method. It is noted that the Constraint Index is determined with the hydrogen form of the zeolite, but that the property is believed to be an attribute of the crystal structure.

Constraint Index (CI) values for some typical materials are shown in Table A.

TABLE A

| ZEOLITE | CI | (at test temperature) |
|---|---|---|
| ZSM-4 | 0.5 | (316° C.) |
| ZSM-5 | 6–8.3 | (371° C.–316° C.) |
| ZSM-11 | 5–8.7 | (371° C.–316° C.) |
| ZSM-12 | 2.3 | (316° C.) |
| ZSM-20 | 0.5 | (371° C.) |
| ZSM-22 | 7.3 | (427° C.) |
| ZSM-23 | 9.1 | (427° C.) |
| ZSM-34 | 50 | (371° C.) |
| ZSM-35 | 4.5 | (454° C.) |
| ZSM-38 | 2 | (510° C.) |
| ZSM-48 | 3.5 | (538° C.) |
| ZSM-50 | 2.1 | (427° C.) |
| TMA Offretite | 3.7 | (316° C.) |
| TEA Mordenite | 0.4 | (316° C.) |
| Clinoptilolite | 3.4 | (510° C.) |
| Mordenite | 0.5 | (316° C.) |
| REY | 0.4 | (316° C.) |
| Amorphous Silica-alumina | 0.6 | (538° C.) |
| Dealuminized Y | 0.5 | (510° C.) |
| Erionite | 38 | (316° C.) |
| Zeolite Beta | 0.6–2.0 | (316° C.–399° C.) |

The above-described Constraint Index is an important and even critical definition of thiose zeolites which are useful in the instant invention. The very nature of this parameter and the recited technique by which it is determined, however, admit of the possibility that a given zeolite can be tested under somewhat different conditions and thereby exhibit different Constraint Indices. Constraint Index seems to vary somewhat with severity of operations (conversion) and the presence or absence of binders. Likewise, other variables, such as crystal size of the zeolite, the presence of occluded contaminants, etc., may affect the Constraint Index. Therefore, it will be appreciated that it may be possible to so select test conditions, e.g. temperature, as to establish more than one value for the Constraint Index of a particular zeolite. This explains the range of Constraint Indices for some zeolites, such as ZSM-5, ZSM-11 and Beta.

It is to be realized that the above CI values typically characterize the specified zeolites, but that such values are the cumulative result of several variables useful in the determination and calculation thereof. Thus, for a given zeolite exhibiting a CI value within the range of 1 to 12, depending on the temperature employed during the test method within the range of 290° C. to about 538° C., with accompanying conversion between 10% and 60%, the CI may vary within the indicated range of 1 to 12. Likewise, other variables such as the crystal size of the zeolite, the presence of possibly occluded contaminants and binders intimately combined with the zeolite may affect the CI. It will accordingly be understood by those skilled in the art that the CI, as utilized herein, while affording a highly useful means for characterizing the zeolites of interest is approximate, taking into consideration the manner of its determination, with the possibility, in some instances, of compounding variable extremes. However, in all instances, at a temperature within the above-specified range of 290° C. to about 538° C., the CI will have a value for any given zeolite of interest herein within the approximate range of 1 to 12.

The class of highly siliceous zeolites defined herein is exemplified by ZSM-5, ZSM-11, ZSM-12, ZSM-22, ZSM-23, ZSM-35, ZSM-38, ZSM-48, ZSM-50, and other similar materials.

U.S. Pat. No. 3,702,886 describing and claiming ZSM-5 is incorporated herein by reference.

ZSM-11 is more particularly described in U.S. Pat. No. 3,709,979, the entire content of which is incorporated herein by reference.

ZSM-12 is more particularly described in U.S. Pat. No. 3,832,449, the entire content of which is incorporated herein by reference.

ZSM-22 is more particularly described in U.S. Pat. No. 4,046,859, the entire content of which is incorporated herein by reference.

ZSM-23 is more particularly described in U.S. Pat. No. 4,076,842, the entire content of which is incorporated herein by reference.

ZSM-35 is more particularly described in U.S. Pat. No. 4,016,245, the entire content of which is incorporated herein by reference.

ZSM-38 is more particularly described in U.S. Pat. No. 4,046,859, the entire content of which is incorporated herein by reference.

ZSM-48 is more particularly described in U.S. Pat. No. 4,397,827, the entire content of which is incorporated herein by reference.

Conventional Zeolite ZSM-50 is characterized, in terms of moles of oxides per 100 moles of silica on an anhydrous basis, as follows:

$$(0-10)M_{2/n}O:(1-5)Al_2O_3:(100)SiO_2$$

wherein M is at least one cation having a valence n, and wherein the zeolite is characterized by a distinctive X-ray diffraction pattern substantially as shown in Table B.

TABLE B

| Interplanar d-Spacing (A) | Relative Intensity, $I/I_o$ |
|---|---|
| 20.1 ± .03 | W |
| 11.1 ± .17 | S |
| 10.1 ± .16 | M |
| 9.7 ± .14 | W |
| 5.77 ± .09 | W |
| 5.61 ± .09 | W |
| 4.64 ± .07 | M |
| 4.35 ± .07 | M |

TABLE B-continued

| Interplanar d-Spacing (A) | Relative Intensity, I/I$_o$ |
|---|---|
| 4.30 ± .07 | VS |
| 4.00 ± .06 | S |
| 3.85 ± .06 | M |
| 3.70 ± .06 | M |
| 3.42 ± .05 | W |
| 3.35 ± .05 | W |
| 3.27 ± .05 | M |
| 3.24 ± .05 | W |
| 2.94 ± .04 | W |
| 2.53 ± .04 | W |

These values were determined by standard techniques. The radiation was the K-alpha doublet of copper and a diffractometer equipped with a scintillation counter and an associated computer was used. The peak heights, I, and the positions as a function of 2 theta, where theta is the Bragg angle, were determined using algorithms on the computer associated with the spectrometer. From these, the relative intensities, 100 I/I$_o$, where I$_o$ is the intensity of the strongest line or peak, and d-spacing the interplanar spacing in Angstrom Units (A), corresponding to the recorded lines, were determined. In Table B, the relative intensities are given in terms of the symbols W=weak, M=medium, S=strong and VS=very strong. In terms of intensities, these may be generally designated as follows:

W=0-20
M=20-40
S=40-60
VS=60-100

In the conventionally synthesized form, Zeolite ZSM-50 has a formula, on an anhydrous basis and in terms of moles of oxides per 100 moles of silica, as follows:

$$(0-4)R_2O:(0-10)M_{2/n}O:(1-5)Al_2O_3:(100)SiO_2$$

wherein M is an alkali or alkaline earth metal, n is the valence of M, and R is an organic cation of a diquaternary directing agent compound generally expressed by the following formula:

$$X(CH_3)_3N(CH_2)_6N(CH_3)_3X$$

wherein X is an anion, e.g. halide, such as iodide.

Conventional Zeolite ZSM-50 can be prepared from a reaction mixture containing sources of an alkali or alkaline earth metal oxide, an oxide of aluminum, an oxide of silicon, an organic cation and water and having a composition, in terms of mole ratios of oxides, within the following ranges:

| Reactants | Useful | Preferred |
|---|---|---|
| SiO$_2$/Al$_2$O$_3$ | 20-100 | 30-90 |
| OH$^-$/SiO$_2$ | 0.1-0.6 | 0.1-0.3 |
| R/SiO$_2$ | 0.05-0.6 | 0.1-0.3 |
| M/SiO$_2$ | 0.01-1.0 | 0.1-0.6 | wherein M is an alkali or alkaline earth metal and R is an organic cation derived from the above-identified diquaternary directing agent compound.

Crystallization of conventional Zeolite ZSM-50 can be carried out at either static or stirred condition in a suitable reactor vessel, such as for example, polypropylene jars or teflon lined or stainless steel autocllaves. The total useful range of temperatures for crystallization is from about 100° C. to about 200° C. for a time of about 48 hours to about 15 days. Thereafter, the crystals are separated from the liquid and recovered.

It is preferred to use a zeolite selected from the group consisting of ZSM-5, ZSM-11, ZSM-12, ZSM-22, ZSM-23, ZSM-35, and ZSM-50 as the zeolite component of the catalyst used in the process of this invention. ZSM-5 is the particularly preferred zeolite, characterized by high activity and favorable selectivity for isobutane.

It is desirable in this invention to employ variants of the zeolite that have high acid activity when these are available. For example, a zeolite having a lower silica-to-alumina ratio is preferred to one of higher ratio since the acid activity as measured by the "alpha test" of the former is higher. The "alpha test", which provides a measure of the relative rate constant of the zeolite for cracking normal hexane (i.e. the alpha value), is described by Miale et al. in Journal of Catalysis, Volume 6, No. 2, October 1966, and is herein incorporated by reference as if fully set forth.

The specific zeolites described, when prepared in the presence of organic cations, are substantially catalytically inactive, possibly because the intra-crystalline free space is occupied by organic species from the forming solution. These organic templates are removed by heating in an inert atmosphere at 1000° F. for one hour, for example, followed by base exchange with ammonium salts followed by calcination at 1000° F. in air. If binder is used with the zeolite, as described hereinbelow, the activation step just described may be conducted after compositing with the binder.

The zeolite component of the catalyst may be the sole component, i.e. it may be shaped into pellets using known methods, and in such shaped form it can serve as an effective catalyst in the process of this invention. For better particle properties, or for ease of formation of shaped particles, however, it is often advantageous to composite the zeolite powder with a binder, such as for example with alumina, and to form the catalyst particles by extrusion or other methods known in the art. Extrudate particles containing about 65 wt% zeolite and 35 wt% alumina binder exemplify a catalyst suitable for use in the process of the present invention.

The zeolite component of the catalyst is converted to the hydrogen form prior to use in the process of this invention, since the zeolite is highly active in that form. As known to those skilled in the art, this conversion may be accomplished by base exchange with ammonium salts to convert the zeolite to the ammonium form, followed by drying and calcination in air at 1000° F., for example, to convert the ammonium form to the hydrogen form. As used in the present invention, the designation H-ZSM-5, H-ZSM-50, etc. refer to the zeolite in the hydrogen form and without a hydrogenation-dehydrogenation (H/D) metal. Pt-ZSM-5, Zn-ZSM-5, etc. refer to the zeolite in the hydrogen form with the designated metal H/D component present.

Although the process of this invention can be practised in the absence of an H/D component, in some instances the presence of such component induces an increase in activity and/or selectivity. The data in the examples shown hereinunder indicate that platinum metal acts in such fashion. Other metals which can facilitate hydrogenation-dehydrogenation or olefin disproportionation, such as the Fe or Pt metals of Group VIII of the Periodic Table, metals of Group IIb, titanium, vanadium, chromium, molybdenum, tungsten, rhenium and gallium, may be useful. (Chem. Rubber Handbook, 45th Ed., back cover).

EXAMPLES

The examples which follow illustrate the invention. However, they are not to be construed as limiting the scope of the invention, which scope is defined by the entire content of this specification, including appended claims.

The examples were all run in a laboratory catalytic apparatus consisting of a stainless steel downflow reactor 10 inches long and having an internal diameter of 7/16 inch. The catalyst was loaded into the lower four inches on a one inch bed of Vycor. The upper 5 inches was loaded with Vycor and served as the preheater. The catalysts were pretreated in air at 900° F. prior to use. If a metal was present, air calcination was followed by hydrogen reduction at 900° F. Material balances were made by collection of the product stream in a liquid nitrogen-cooled trap and subsequent expansion into a precalibrated, constant volume glass system. Liquid and gas analysis were by gas chromatography. The propane charge contained 99.5 wt% propane and about 0.3–0.5 wt% propylene as impurity. Except for Example 19, which is not within the scope of this invention, none of the examples employed added hydrogen.

EXAMPLES 1–15

The catalyst used in these examples was H-ZSM-5 having a silica-to-alumina ratio of 70:1, composited with alumina binder and extruded to form 1/16 inch diameter particles. The zeolite to binder weight ratio was 65:35. The charge of catalyst used in Example 1 was used for all of the remaining examples 2–15, with no regneration. The results are shown in Tables I, II, and III.

TABLE I

| CONVERSION OF PROPANE OVER H-ZSM-5 | | | | | |
|---|---|---|---|---|---|
| EXAMPLE NO. | 1 | 2 | 3 | 4 | 5 |
| TEMPERATURE, °F. | 651.00 | 676.00 | 676.00 | 675.00 | 675.00 |
| WHSV | 1.00 | 1.00 | 1.10 | 1.10 | 1.00 |
| MATERIAL BALANCE | 100.99 | 101.37 | 98.19 | 106.25 | 117.87 |
| T.O.S., HRS. | 5.30 | 28.60 | 52.60 | 120.10 | 144.10 |
| PRODUCT DISTRIBUTION, WT % | | | | | |
| C1 | 0.23 | 0.70 | 0.69 | 0.63 | 0.75 |
| C2 | 0.54 | 1.65 | 1.62 | 1.48 | 1.72 |
| C2= | 0.00 | 0.00 | 0.00 | 0.00 | 0.00 |
| C3 | 95.55 | 87.94 | 87.99 | 89.08 | 87.54 |
| C3= | 0.00 | 0.00 | 0.00 | 0.00 | 0.00 |
| ISO-C4 | 1.47 | 3.74 | 3.75 | 3.38 | 3.84 |
| N-C4 | 2.21 | 5.22 | 5.23 | 4.83 | 5.35 |
| C4= | 0.00 | 0.00 | 0.00 | 0.00 | 0.00 |
| ISO-C5 | 0.00 | 0.47 | 0.44 | 0.40 | 0.49 |
| N-C5 | 0.00 | 0.28 | 0.28 | 0.20 | 0.30 |
| WT % CONVERSION TO C1-C4 | 4.45 | 12.06 | 12.01 | 10.92 | 12.46 |
| SELECTIVITY, WT % | 4.45 | 11.31 | 11.29 | 10.32 | 11.67 |
| C1 + C2 | 17.30 | 19.49 | 19.23 | 19.32 | 19.82 |
| ISO-C4 | 33.03 | 31.01 | 31.22 | 30.95 | 30.82 |
| N-C4 | 49.66 | 43.28 | 43.55 | 44.23 | 42.94 |
| C5'S | TRACE | 6.22 | 6.00 | 5.49 | 6.34 |
| C6+'S | 0.00 | 0.00 | 0.00 | 0.00 | 0.00 |

TABLE II

| CONVERSION OF PROPANE OVER H-ZSM-5 | | | | | |
|---|---|---|---|---|---|
| EXAMPLE NO. | 6 | 7 | 8 | 9 | 10 |
| TEMPERATURE, °F. | 675.00 | 700.00 | 700.00 | 700.00 | 700.00 |
| WHSV | 1.00 | 1.00 | 1.00 | 1.10 | 1.00 |
| MATERIAL BALANCE | 101.21 | 111.13 | 110.22 | 102.53 | 117.87 |
| T.O.S., HRS. | 172.90 | 192.10 | 216.10 | 292.60 | 312.10 |
| PRODUCT DISTRIBUTION, WT % | | | | | |
| C1 | 0.72 | 1.38 | 1.41 | 1.23 | 1.48 |
| C2 | 1.66 | 3.35 | 3.55 | 2.89 | 3.46 |
| C2= | 0.00 | 0.00 | 0.00 | 0.00 | 0.00 |
| C3 | 88.16 | 76.07 | 75.16 | 80.99 | 77.97 |
| C3= | 0.00 | 0.00 | 0.00 | 0.00 | 0.00 |
| ISO-C4 | 3.65 | 6.25 | 6.52 | 5.68 | 6.47 |
| N-C4 | 5.09 | 8.21 | 8.47 | 7.64 | 8.53 |
| C4= | 0.00 | 0.00 | 0.00 | 0.00 | 0.00 |
| ISO-C5 | 0.45 | 1.32 | 1.42 | 1.00 | 1.33 |
| N-C5 | 0.27 | 0.87 | 0.88 | 0.58 | 0.77 |
| C6 + PAR + CYCLOPAR | 0.00 | 2.10 | 1.93 | 0.00 | 0.00 |
| C + 6 AROMATICS | 0.00 | 0.46 | 0.64 | 0.00 | 0.00 |
| TOTAL C6+ PRODUCTS | 0.00 | 2.56 | 2.57 | 0.00 | 0.00 |
| WT % CONVERSION TO C1-C4 | 11.84 | 23.93 | 24.84 | 19.01 | 22.03 |
| SELECTIVITY, WT % | 11.12 | 19.19 | 19.94 | 17.43 | 19.93 |
| C1 + C2 | 20.10 | 19.77 | 19.97 | 21.67 | 22.42 |
| ISO-C4 | 30.83 | 26.12 | 26.27 | 29.88 | 29.37 |
| N-C4 | 42.99 | 34.31 | 34.10 | 40.19 | 38.72 |
| C5'S | 6.08 | 9.15 | 9.26 | 8.31 | 9.53 |
| C6+'S | 0.00 | 10.70 | 10.35 | TRACE | TRACE |

TABLE III

| CONVERSION OF PROPANE OVER H-ZSM-5 | | | | | |
|---|---|---|---|---|---|
| EXAMPLE NO. | 11 | 12 | 13 | 14 | 15 |
| TEMPERATURE, °F. | 700.00 | 700.00 | 701.00 | 701.00 | 675.00 |
| WHSV | 1.00 | 1.10 | 1.00 | 1.10 | 1.00 |
| MATERIAL BALANCE | 108.13 | 103.20 | 105.56 | 104.06 | 106.29 |
| T.O.S., HRS. | 336.10 | 360.10 | 384.10 | 456.10 | 480.10 |
| PRODUCT DISTRIBUTION, WT % | | | | | |
| C1 | 1.47 | 1.38 | 1.45 | 1.33 | 0.65 |
| C2 | 3.61 | 3.24 | 3.51 | 3.20 | 1.42 |
| C2= | 0.00 | 0.00 | 0.00 | 0.00 | 0.00 |
| C3 | 77.60 | 79.11 | 77.73 | 79.20 | 89.36 |
| C3= | 0.00 | 0.00 | 0.00 | 0.00 | 0.00 |
| ISO-C4 | 6.56 | 6.20 | 6.65 | 6.15 | 3.18 |
| N-C4 | 8.59 | 8.19 | 8.50 | 8.22 | 4.70 |
| C4= | 0.00 | 0.00 | 0.00 | 0.00 | 0.00 |
| ISO-C5 | 1.37 | 1.20 | 1.36 | 1.20 | 0.41 |

TABLE III-continued

CONVERSION OF PROPANE OVER H-ZSM-5

| EXAMPLE NO. | 11 | 12 | 13 | 14 | 15 |
|---|---|---|---|---|---|
| N-C5 | 0.79 | 0.68 | 0.80 | 0.70 | 0.27 |
| WT % CONVERSION | 22.40 | 20.89 | 22.27 | 20.80 | 10.64 |
| TO C1-C4 | 20.24 | 19.01 | 20.12 | 18.90 | 9.95 |
| SELECTIVITY, WT % | | | | | |
| C1 + C2 | 22.68 | 22.12 | 22.27 | 21.78 | 19.45 |
| ISO-C4 | 29.29 | 29.68 | 29.86 | 29.57 | 29.89 |
| N-C4 | 38.35 | 39.21 | 38.17 | 39.52 | 44.17 |
| C5'S | 9.64 | 9.00 | 9.70 | 9.13 | 6.39 |
| C6+'S | TRACE | TRACE | TRACE | TRACE | 0.00 |

EXAMPLES 16-21

The Pt-ZSM-50 catalyst used in these examples was prepared from an H-ZSM-50 zeolite having a silica-to-alumina ratio of 32:1. The zeolite was impregnated with tetrammine platinum dichloride using the incipient wetness technique. The final catalyst contained 2 wt% platinum. The pure zeolite (no binder) was meshed to 20×60 particle size and charged to the reactor for Example 16. Runs 17-21 used the same charge of catalyst without regeneration. Example 19, not within the scope of this invention, is shown to illustrate the deleterious effect of added hydrogen.

TABLE IV

CONVERSION OF PROPANE OVER PT-ZSM-50

| EXAMPLE NO. | 16 | 17 | 18 | 19 | 20 | 21 |
|---|---|---|---|---|---|---|
| TEMPERATURE, °F. | 649.00 | 699.00 | 798.00 | 700.00 | 800.00 | 850.00 |
| WHSV | 1.20 | 1.00 | 1.10 | 1.20 | 1.10 | 0.60 |
| H2/HC MOL RATIO | 0.00 | 0.00 | 0.00 | 2.10 | 0.00 | 0.00 |
| MATERIAL BAL. | 92.80 | 103.81 | 105.88 | 90.86 | 91.68 | 103.89 |
| T.O.S., HRS. | 39.50 | 63.20 | 87.20 | 93.70 | 113.60 | 118.60 |
| PRODUCT DISTRIBUTION, WT % | | | | | | |
| C1 | 0.05 | 0.05 | 0.41 | 0.23 | 0.25 | 0.54 |
| C2 | 0.57 | 1.25 | 3.80 | 0.89 | 2.66 | 1.05 |
| C2= | 0.00 | 0.00 | 0.00 | 0.00 | 0.00 | 0.03 |
| C3 | 91.89 | 89.07 | 79.77 | 98.81 | 83.95 | 93.26 |
| C3= | 0.00 | 0.00 | 0.00 | 0.00 | 0.00 | 0.39 |
| ISO-C4 | 3.44 | 4.17 | 5.24 | 0.07 | 4.80 | 1.90 |
| N-C4 | 3.62 | 4.80 | 7.27 | 0.00 | 6.14 | 2.83 |
| C4= | 0.00 | 0.00 | 0.00 | 0.00 | 0.00 | 0.00 |
| ISO-C5 | 0.34 | 0.50 | 0.89 | 0.00 | 0.41 | 0.00 |
| N-C5 | 0.08 | 0.16 | 0.47 | 0.00 | 0.22 | 0.00 |
| C6 + PAR + CYCLOP | 0.00 | 0.00 | 0.98 | 0.00 | 0.38 | 0.00 |
| C6 + AROMATICS | 0.00 | 0 | 1.15 | 0.00 | 1.19 | 0.00 |
| TOTAL C6 + PRODS. | 0.00 | 0.00 | 2.13 | 0.00 | 1.57 | 0.00 |
| WT % CONVERSION | 8.11 | 10.93 | 20.23 | 1.19 | 16.05 | 6.74 |
| TO C1-C4 | 7.69 | 10.27 | 16.72 | 1.19 | 13.86 | 6.74 |
| SELECTIVITY, WT % | | | | | | |
| C1 + C2'S | 7.62 | 11.89 | 20.81 | 94.12 | 18.13 | 24.04 |
| ISO-C4 | 42.42 | 38.15 | 25.90 | 5.88 | 29.91 | 28.19 |
| N-C4 | 44.64 | 43.82 | 35.94 | 0.00 | 38.26 | 41.99 |
| C5'S | 5.18 | 6.04 | 6.77 | 0.00 | 3.93 | 0.00 |
| C6+'S | 0.00 | 0.00 | 10.58 | 0.00 | 9.78 | 0.00 |

EXAMPLES 22-24

The catalyst for Example 22 was prepared, charged and used in the same manner as the catalyst for Example 16 except that H-ZSM-5 having a silica-to-alumina ratio of 40 was used instead of H-ZSM-50. As in Example 16, no binder was used. The catalyst of Example 22 was used, without regeneration, for Examples 23 and 24.

TABLE V

CONVERSION OF PROPANE OVER PT-ZSM-5

| EXAMPLE NO. | 22 | 23 | 24 |
|---|---|---|---|
| TEMPERATURE, °F. | 725.00 | 601.00 | 625.00 |
| WHSV | 1.10 | 1.20 | 0.50 |
| MATERIAL BALANCE | 104.73 | 91.27 | 111.43 |
| T.O.S., HRS. | 22.50 | 29.30 | 26.70 |
| PRODUCT DISTRIBUTION, WT % | | | |
| C1 | 2.95 | 0.13 | 0.55 |
| C2 | 47.72 | 1.17 | 4.10 |
| C2= | 0.00 | 0.00 | 0.00 |
| C3 | 29.47 | 88.30 | 76.48 |
| C3= | 0.00 | 0.00 | 0.00 |
| ISO-C4 | 2.56 | 4.62 | 6.98 |
| N-C4 | 2.95 | 5.19 | 7.84 |
| C4= | 0.00 | 0.00 | 0.00 |
| ISO-C5 | 0.27 | 0.40 | 1.31 |
| N-C5 | 0.20 | 0.20 | 0.82 |
| C5= | 0.02 | 0.00 | 0.00 |
| C6 + CYCLOPAR | 0.99 | 0.00 | 1.81 |
| C6+ AROMATICS | 12.87 | 0.00 | 0.11 |
| TOTAL C6+ PRODUCTS | 13.86 | 0.00 | 1.92 |
| WT % CONVERSION | 70.53 | 11.70 | 23.52 |
| TO C1-C4 | 56.19 | 11.11 | 19.47 |
| SELECTIVITY, WT % | | | |
| C1 + C2 | 71.80 | 11.11 | 19.77 |
| ISO-C4 | 3.63 | 39.49 | 29.68 |
| N-C4 | 4.18 | 44.36 | 33.33 |
| C5'S | 0.69 | 5.13 | 9.06 |
| C6+'S | 19.05 | 0.00 | 8.16 |
| C4+'S | 28.20 | 88.89 | 80.23 |

EXAMPLE 25

Example 1 is repeated but H-ZSM-11 is substituted for the H-ZSM-5 used in that example. The results are substantially the same.

EXAMPLES 26–28

In these examples the hydrogen form of the zeolite is composited with 35 wt% alumina and extruded to form 1/16 inch diameter extrudate. Platinum was impregnated on the catalyst using the incipient wetness technique using chloroplatinic acid in a concentration to provide the desired content of platinum. The catalyst of Example 26 was made with H-ZSM-22 having a silica-to-alumina ratio of 82 and the catalyst had a Pt content of 0.57 wt%. The catalyst of Example 27 was made with H-ZSM-23 having a silica-to-alumina ratio of 115, and the catalyst had a platinum ciontent of 0.05 wt%. The catalyst of Example 28 was made with H-ZSM-35 having a silica-to-alumina ratio of 13, and the catalyst had a platinum content of 0.59 wt% platinum.

All three catalysts were tested as described in Example 1 using 800 psig pressure and 1 WHSV. The results are shown in Table VI.

TABLE VI

CONVERSION OF PROPANE OVER ZEOLITES ZSM-22, ZSM-23, ZSM-35

| EXAMPLE NO. | 26 | 27 | 28 |
|---|---|---|---|
| CATALYST | Pt-ZSM-22 | Pt-ZSM-23 | Pt-ZSM-35 |
| TEMPERATURE, °F. | 700 | 748 | 750 |
| WT % CONVERSION | 10 | 11 | 8 |
| SELECTIVITIES | | | |
| C1 + C2 | 40 | 35 | 38 |
| ISO-C4 | 16 | 15 | 6 |
| M-C4 | 19 | 20 | 12 |
| C5+'S | 25 | 30 | 42 |

EXAMPLE 29

In this example the catalyst was prepared from 26 grams NH4-ZSM-5 having a silica-to-alumina ratio of 40. This was exchanged once with a mixture of 10 grams $NH_4NO_3$ and 3 g $ZnCl_2$ in 100 cc of water at 100° F. for 17 hours. It was rinsed and dried at 100° F. for 22 hours. It was meshed 20×60 and calcined in air at 1000° F. for 12 hours. The resultant binder-free catalyst had 0.38 wt% Zn.

The catalyst was loaded into the reactor and tested as in Example 1 at 800 psig and at 0.4 WHSV. The conversion found was 16 wt%, with the following selectivities:

| | |
|---|---|
| C1 + C2 | 21 wt % |
| ISO-C4 | 32 wt % |
| N-C4 | 40 wt % |
| C5+'S | 7 wt % |

What is claimed is:

1. A process for the production of butanes from propane, which process comprises contacting a propane feed in the absence of added hydrogen and at a pressure of at least about 50 psig with a catalyst comprising a crystalline zeolite having a silica-to-alumina ratio of at least 12 and a Constraint Index of 1 to 12 measured at a temperature within the range of 290° C. to about 538° C., said contacting being conducted under a combination of conditions of temperature, pressure, and WHSV effective to convert up to about 25 wt% of said propane to a mixture of hydrocarbons that contains butanes in an amount equal to at least 35 wt% of said converted propane, and, recovering said butanes.

2. The process of claim 1 wherein said catalyst includes a hydrogenation-dehydrogenation component and said temperature is 500° F. to 900° F., said pressures is 50 to 1500 psig, said WHSV is 0.1 to 10, and said conversion of propane to butanes is about 10 to about 25 wt% of said propane.

3. The process of claim 2 wherein said hydrogenation-dehydrogenation component is a platinum group metal.

4. The process of claim 1 wherein said zeolite is selected from the group consisting of zeolites having the structure of ZSM-5, ZSM-11, ZSM-12, ZSM-22, ZSM-23, ZSM-35, and ZSM-50.

5. The process of claim 2 wherein said zeolite is selected from the group consisting of zeolites having the structure of ZSM-5, ZSM-11, ZSM-12, ZSM-22, ZSM-23, ZSM-35, and ZSM-50.

6. The process of claim 3 wherein said zeolite is selected from the group consisting of zeolites having the structure of ZSM-5, ZSM-11, ZSM-12, ZSM-22, ZSM-23, ZSM-35, and ZSM-50.

7. The process of claim 5 wherein said hydrogenation-dehydrogenation component is a platinum group metal.

8. The process of claim 1 including the steps of recovering and recycling unconverted propane.

9. The process of claim 2 including the steps of recovering and recycling unconverted propane.

10. The process of claim 1 or 2 or 3 or 4 or 5 or 6 or 7 or 8 or 9 wherein said zeolite is ZSM-5.

* * * * *